United States Patent [19]
Mabuchi et al.

[11] Patent Number: 5,635,448
[45] Date of Patent: Jun. 3, 1997

[54] HERBICIDAL COMPOSITION FOR UPLAND FARMING AND WEEDING METHOD

[75] Inventors: Tsutomu Mabuchi, Osakasayama; Takashi Ootsuka, Tondabayashi; Takamichi Konno, Osakasayama, all of Japan

[73] Assignee: Asamura Patent Office, Tokyo, Japan

[21] Appl. No.: 672,502

[22] Filed: Jun. 28, 1996

Related U.S. Application Data

[63] Continuation of Ser. No. 221,932, Apr. 1, 1994, abandoned.

[30] Foreign Application Priority Data

Apr. 4, 1993 [JP] Japan ................... 5-101920

[51] Int. Cl.$^6$ ................................. A01N 43/56
[52] U.S. Cl. .................. 504/139; 504/133; 504/134; 504/135
[58] Field of Search ...................... 504/135, 133, 504/139, 134

[56] References Cited

U.S. PATENT DOCUMENTS

| | | |
|---|---|---|
| 5,032,161 | 7/1991 | Pieper et al. ................... 65/335 |
| 5,112,384 | 5/1992 | Miura et al. ................... 548/376 |

FOREIGN PATENT DOCUMENTS

| | | |
|---|---|---|
| 361114 | 4/1990 | European Pat. Off. . |
| 447055 | 9/1991 | European Pat. Off. . |

OTHER PUBLICATIONS

Chemical Patents Index, Documentation Abstracts Journal, Week 9215, Derwent Publication Ltd. AN 92–118314 & JP-A-04 059 706, Feb. 26, 1992.

Chemical Patents Index, Documentation Abstracts Journal, Week 9150, Derwent Publications Ltd., AN 91–365775 & JP-A-03 246 204, Nov. 1, 1991.

The Agrochemicals Handbook, 3rd Edition. Royal Society of Chemistry, England, 1991 p. A0669.

*Primary Examiner*—S. Mark Clardy
*Assistant Examiner*—Brian G. Bernbenick
*Attorney, Agent, or Firm*—Cushman Darby & Cushman, Intellectual Property Group of Pillsbury Madison & Sutro, L.L.P.

[57] ABSTRACT

A herbicidal composition for upland farming which can control weeds that have been difficult to control, for example, cleavers, chickweed, birdseye speedwell and violet, said composition containing as active ingredients a 3-substituted phenylpyrazole derivative represented by the general formula (I):

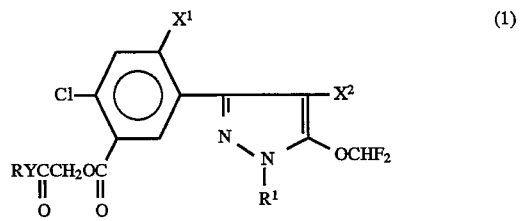

(wherein R is a hydrogen atom, a $C_{1-6}$ alkyl group, a $C_{3-6}$ cycloalkyl group, a $C_{1-6}$ haloalkyl group, a $C_{2-6}$ alkenyl group or a $C_{2-6}$ alkynyl group, $R^1$ is a $C_{1-6}$ alkyl group, $X^1$ and $X^2$, which may be the same or different, are halogen atoms, and Y is an oxygen atom or a sulfur atom) and at least one compound selected from the group consisting of sulfonylurea derivatives, phenylurea derivatives and phenoxy fatty acid derivatives; and a weeding method using said composition.

12 Claims, 2 Drawing Sheets

HERBICIDAL COMPOSITION FOR UPLAND FARMING AND WEEDING METHOD

This is a continuation of application Ser. No. 08/221,932, filed on Apr. 1, 1994, which was abandoned upon the filing hereof.

BACKGROUND OF THE INVENTION

1. Field of the Invention

This invention relates to a herbicidal composition for upland farming which contains as active ingredients a 3-substituted phenylpyrazole derivative represented by the general formula (I):

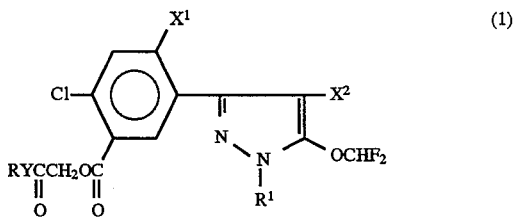

(wherein R is a hydrogen atom, a $C_{1-6}$ alkyl group, a $C_{3-6}$ cycloalkyl group, a $C_{1-6}$ haloalkyl group, a $C_{2-6}$ alkenyl group or a $C_{2-6}$ alkynyl group, $R^1$ is a $C_{1-6}$ alkyl group, $X^1$ and $X^2$, which may be the same or different, are halogen atoms, and Y is an oxygen atom or a sulfur atom) and at least one compound selected from the group consisting of sulfonylurea derivatives, phenylurea derivatives and phenoxy fatty acid derivatives; and a weeding method.

2. Related Art

At present, various herbicides are used for controlling weeds in cultivation of crops (e.g. wheat, barley, soybean and corn) by upland farming. The weeds to be controlled in the upland farming are various in kind and their emergence period is long. Therefore, it is necessary to use a herbicide which has a wide weed control spectrum, is harmless to the crops, and exhibits a marked herbicidal effect even at a low dosage.

SUMMARY OF THE INVENTION

In view of such conditions, the present inventors earnestly investigated in order to develop a herbicide which has a wide weed control spectrum, prevents the emergence of weeds for a long period of time, is harmless to crops, and exhibits a herbicidal effect even at a low dosage. Consequently, the present inventors found that the combination of 3-substituted phenylpyrazole derivative of the above general formula (I) and at least one compound selected from the group consisting of sulfonylurea derivatives, phenylurea derivatives and phenoxy fatty acid derivatives brings about a synergistic effect unexpectedly larger than that obtained by using each of the derivative and the compounds alone, and hence permits reduction of the dosage and expansion of the weed control spectrum, whereby the present invention has been accomplished.

DETAILED DESCRIPTION OF PREFERRED EMBODIMENTS

Figure 1:
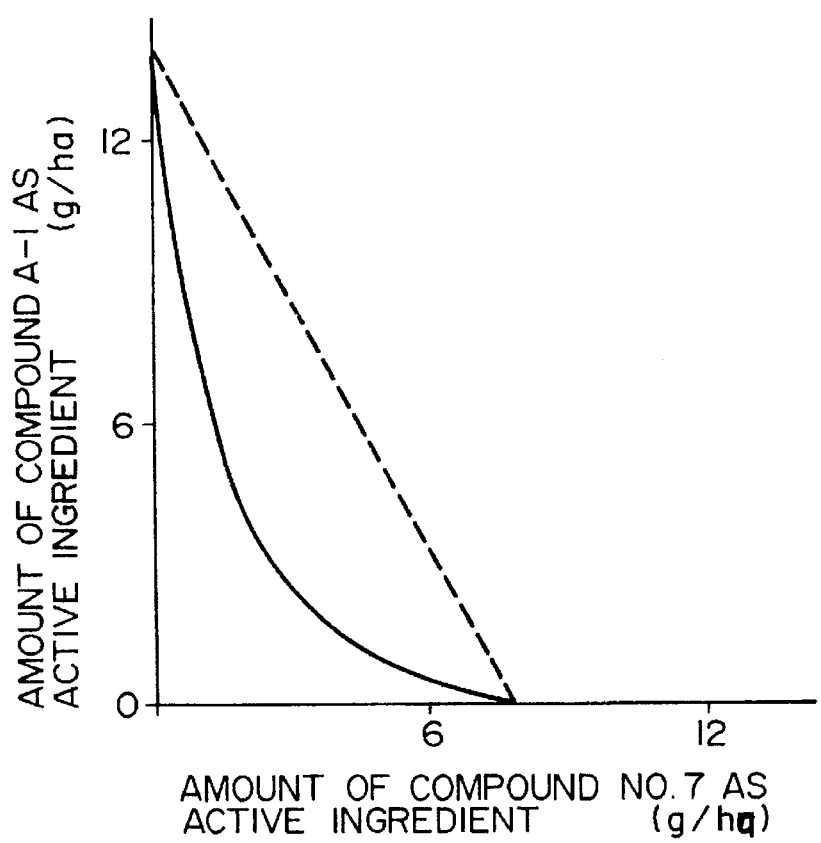
FIG. 1 is a graph which shows the synergistic effect of the herbicidal composition for upland farming of the present invention by isobole analysis and illustrates the results shown in Table 5.

The 3-substituted phenylpyrazole derivative of the general formula (I), i.e., one of the active ingredients used in the present invention, is a compound well known as a herbicide in Japanese Patent Unexamined Publication No. 4-211065.

In the definition of the substituents of the 3-substituted phenylpyrazole derivative of the general formula (I) of the present invention, the prefix "halo" is used for expressing that a group contains one or more halogen atoms selected from chlorine, fluorine, bromine and iodine atoms. For example, the term "haloalkyl group" means a substituted alkyl group having as the substituent(s) one or more halogen atoms which may be the same or different and are selected from the group consisting of chlorine atom, fluorine atom, bromine atom and iodine atom.

Preferable examples of substituent for R are alkyl groups such as methyl, ethyl, n-propyl, i-propyl, n-butyl, s-butyl, i-butyl, t-butyl, n-pentyl, n-hexyl, etc. Of these, methyl group and ethyl group are particularly preferable.

Preferable examples of substituent for $R^1$ are alkyl groups such as methyl, ethyl, n-propyl, i-propyl, n-butyl, s-butyl, i-butyl, t-butyl, n-pentyl, n-hexyl, etc. Of these, methyl group is particularly preferable.

Preferable examples of substituent for $X^1$ are chlorine or fluorine atoms.

Preferable example of substituent for $X^2$ is chlorine atom.

Preferable example of substituent for Y is a sulfur atom.

Typical examples of said derivative are given in Table 1.

General formula (1):

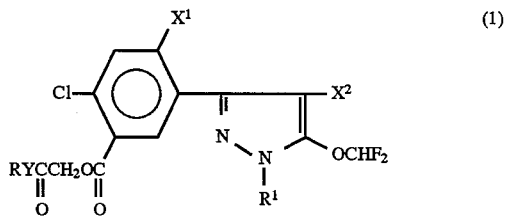

| Compound No. | R | $R^1$ | $X^1$ | $X^2$ | Y | Physical properties |
|---|---|---|---|---|---|---|
| 1 | $CH_3$ | $CH_3$ | Cl | Cl | O | m.p. 74.4° C. |
| 2 | $CH_3$ | $CH_3$ | F | Cl | O | |
| 3 | $CH_3$ | $CH_3$ | Cl | Cl | S | |
| 4 | $CH_3$ | $CH_3$ | F | Cl | S | |
| 5 | $C_2H_5$ | $CH_3$ | Cl | Cl | O | m.p. 57.2° C. |
| 6 | $C_2H_5$ | $CH_3$ | F | Cl | O | nD 1.5362 (23.4° C.) |
| 7 | $C_2H_5$ | $CH_3$ | Cl | Cl | S | nD 1.5763 (20.7° C.) |
| 8 | $C_2H_5$ | $CH_3$ | F | Cl | S | |
| 9 | $i-C_3H_7$ | $CH_3$ | Cl | Cl | O | nD 1.5289 (24.0° C.) |
| 10 | $i-C_3H_7$ | $CH_3$ | F | Cl | O | |
| 11 | $i-C_3H_7$ | $CH_3$ | Cl | Cl | S | nD 1.5684 (20.2° C.) |
| 12 | $i-C_3H_7$ | $CH_3$ | F | Cl | S | |
| 13 | $s-C_4H_9$ | $CH_3$ | Cl | Cl | O | nD 1.5409 (23.4° C.) |
| 14 | $Cl(CH_2)_3$ | $CH_3$ | Cl | Cl | O | |
| 15 | $c-C_6H_{11}$ | $CH_3$ | Cl | Cl | O | nD 1.5477 (28.1° C.) |
| 16 | $CH_2CH=CH_2$ | $CH_3$ | Cl | Cl | O | m.p. 45.4° C. |
| 17 | $CH_2CH=CH_2$ | $CH_3$ | F | Cl | O | |
| 18 | $CH_2C\equiv CH$ | $CH_3$ | Cl | Cl | O | m.p. 79.3° C. |
| 19 | $CH_2C\equiv CH$ | $CH_3$ | F | Cl | O | |

Note: $c-C_6H_{11}$ is a cyclohexyl group.

Examples of compound(s) as the other active ingredient usable in the present invention are given below.

The sulfonylurea derivatives include, for example,

A-1) methyl 2-(4-methoxy-6-methyl-1,3,5-triazin-2-ylcarbamoylsulfamoyl)benzoate (Common name: Metsulfuronmethyl), A-2) 1-(2-chlorophenylsulfonyl)-3-(4-methoxy-6-methyl-1,3,5-triazin-2-yl)urea (Common name: Chlorsulfuron), A-3) methyl 3-(4-methoxy-6-methyl-1,3,5-triazin-2-ylcarbamoylsulfamoyl)thiophen-2-carboxylate (Common name: Thifensulfuron-methyl), A-4) methyl 2-[4-methoxy-6-methyl-1,3,5-triazin-2-yl(methyl)carbamoylsulfamoyl]benzoate (Common name: Tribenuron-methyl), A-5) 1-[2-(2-chloroethoxy)phenylsulfonyl]-3-(4-methoxy-6-methyl-1,3,5-triazin-2-yl)urea (Common name: Triasulfuron), A-6) 1-[(2-methoxycarbonylphenyl)sulfonyl]-3-(4,6-dimethoxypyrimid-2-yl)urea (Common name: Bensulfuronmethyl), A-7) 1-[(2-methoxycarbonylphenyl)sulfonyl]-3-(dimethylpyrimid-2-yl)urea (Common name: Sulfometuronmethyl), A-8) 1-[(2-ethoxycarbonylphenyl)sulfonyl]-3-(4-chloro-6-methoxypyrimid-2-yl)urea (Common name: Chlorimuron-ethyl), A-9) 1-[(3-N,N-dimethylaminocarbonyl)-pyrid-2-yl)-sulfonyl]-3-(4,6-dimethoxypyrimid-2-yl)urea (Common name: Nicosulfuron), A-10) 1-[(3-ethylsulfonyl)-pyrid-2-yl)sulfonyl]-3-(4,6-dimethoxypyrimid-2-yl)urea (Code number: DPX-E9636), A-11) 1-[(2-methoxycarbonylphenyl)sulfonyl]-3-(4,6-bis(difluoromethoxy)pyrimid-2-yl)urea (Common name: Primisulfuron-methyl), A-12) 1-[(4-ethoxycarbonyl-1-methylpyrazol-2-yl)-sulfonyl]-3-(4,6-dimethoxylpyrimid-2-yl)urea (Common name: Pyrazosulfuron-ethyl), A-13) 1-[(2-methoxycarbonylphenyl)sulfonyl]-3-(4-methoxy-6-methylamino-1,3,5-triazin-2-yl)urea (Code number: DPX-A7881), A-14) 1-[(2-methoxyethoxyphenyl)sulfonyl]-3-(4,6-dimethoxy-1,3,5-triazin-2-yl)urea (Common name: Cinosulfuron), A-15) 1-[(3-trifluoroethylpyrid-2-yl)sulfonyl]-3-(4,6-dimethoxypyrimid-2-yl)urea (Common name: Flazasulfuron), and A-16) 1-[(N-methylsulfonyl-N-methylamino)sulfonyl]-3-(4,6-dimethoxypyrimidin-2-yl)urea (Common name: Amidosulfuron).

The phenylurea derivatives include, for example,

B-1. 3-p-cumenyl-1,1-dimethylurea (Common name: Isoproturon),

B-2. 3-(3,4-dichlorophenyl)-1,1-dimethylurea (Common name: Diuron),

B-3. 3-(3,4-dichlorophenyl)-1-methoxy-1-methylurea (Common name: Linuron),

B-4. 3-(4-chlorophenyl)-1,1-dimethylurea (Common name: Monuron),

B-5. 3-(3-chloro-p-tolyl)-1,1-dimethylurea (Common name: Chlorotoluron),

B-6. 1,1-dimethyl-3-phenylurea (Common name: Fenuron),

B-7. 3-(4-chlorophenyl)-1,1,2-trimethylisourea (Common name: Trimeturon),

B-8. 3-(4-chlorophenyl)-1-methoxy-1-methylurea (Common name: Monolinuron),

B-9. 3-(4-chlorophenyl)-1-methyl-1-(1-methylprop-2ynyl)urea (Common name: Buturon), B-10. 3-(4-bromophenyl)-1-methoxy-1-methylurea (Common name: Metobromuron), B-11. 1-(2-methylcyclohexyl)-3-phenylurea (Common name: Siduron), B-12. 1,1-dimethyl-3-(α,α,α-trifluoro-m-tolyl)urea (Common name: Fluometuron), B-13. 1-butyl-3-(3,4-dichlorophenyl)-1-methylurea (Common name: Neburon), B-14. 3-(3-chloro-4-methoxyphenyl)-1,1-dimethylurea (Common name: Metoxuron), B-15. 3-(4-bromo-3-chlorophenyl)-1-methoxy-1-methylurea (Common name: Chlorbromuron), B-16. 3-[3-chloro-4-(chlorodifluoromethylthio)-phenyl]-1,1-dimethylurea (Common name: Fluothiuron), B-17. 3-[4-(4-methoxyphenoxy)phenyl]-1,1-dimethylurea (Common name: Difenoxuron), B-18. 3-[3-(N-t-butylcarbamoyloxy)phenyl]-1,1-dimethylurea (Common name: Karbutilate), B-19. 1-benzoyl-1-(3,4-dichlorophenyl)-3,3-dimethylurea (Common name: Phenobenzuron), and B-20. 1-(1-methyl-1-phenylethyl)-3-p-tolylurea (Common name: Daimuron).

The phenoxy fatty acid derivatives include, for example,

C-1. 4-chloro-o-tolyloxyacetic acid, or sodium or potassium salt thereof (Common name: MCP), C-2. ethyl 4-chloro-o-tolyloxyacetate (Common name: MCP-ethyl), C-3. butyl 4-chloro-o-tolyloxyacetate (Common name: MCP-butyl), C-4. (RS)-2-(4-chloro-o-tolyloxy)propionic acid, or potassium or diethanolamine salt thereof (Common name: Mecoprop), and C-5. 4-(4-chloro-o-tolyloxy)butyric acid or sodium salt thereof (Common name: MCPB).

The compounds exemplified above are not intended in any way to limit the scope of the present invention. In the present invention, any compound may be used so long as it brings about the same effect as that described above when used in admixture with the 3-substituted phenylpyrazole derivative, i.e., one of the active ingredients used in the present invention. For example, the following herbicides may be used.

2-(2-Naphthyloxy)propionanilide (Common name: Naproanilide), N,N-diethyl-2-(1-naphthyloxy)propionamide (Common name: Napropamid), methyl (RS) -2-[4-(2,4-dichlorophenoxy)phenoxy]propionate (Common name: Diclofop-methyl), butyl (RS)-2-[4-(5-trifluoromethyl-2-pyridyloxy)phenoxy]propionate (Common name: Fluazifopbutyl), methyl 2-[4-(3-chloro-5-trifluoromethyl-2pyridyloxy)phenoxy]propionate (Common name: Haloxyfop), 2-propynyl 2-[4-(3,5-dichloro-2-pyridyloxy)phenoxy]propionate (Common name: Chlorazifop-propynyl), 2-propynyl 2-[4-(5-chloro-3-fluoro-2-pyridyloxy)phenoxy]-propionate (Common name: Pyroxofop), ethyl 2-[4-(6-chloro-2-quinoxalyloxy)phenoxy]propionate (Common name: Quizalofop-ethyl), ethyl (±)-2-[4-(6-chloro-1,3-benzoxazol-2-yloxy)phenoxy]propionate (Common name: Fenoxaprop-ethyl), ethyl 2-[4-(6-chloro-2benzothiazolyloxy)phenoxy]propionate (Common name: Fenthiaprop-ethyl), (RS)-2-[2-[4-(3,5-dichloro-2-pyridyloxy)phenoxy]propionyl]-1,2-oxazolidine (Common name: Isoxapyrifop), 2,3,6-trichlorobenzoic acid (Common name: 2,3,6-TBA), 3,6-dichloro-2-methoxybenzoic acid (Common name: Dicamba), 3-amino-2,5-dichlorobenzoic acid (Common name: Chloramben), 3,5,6-trichloro-2-methoxybenzoic acid (Common name: Tricamba), 4'-chloro-2,2-dimethylvaleranilide (Common name: Monalide), 3',4'-dichloropropionanilide (Common name: Propanil), 3',4'-dichloro-2-methylacrylanilide (Common name: Choranocryl), 3',4'-dichlorocyclopropanecarboxyanilide (Common name: Cypromid), N-(3-chloro-p-tolyl)-2methylvaleramide (Common name: Pentanochlor), 3,5-dichloro-N-(1,1- dimethylpropynyl)benzamide (Common name: Propyzamide), N,N-dimethyl-2,2-diphenylacetamide (Common name: Diphenamid), N-1-naphthylphthalamic acid (Common name: Naptalam), 2-bromo-3,3-dimethyl-N-(1-methyl-1phenylethyl)butylamide (Common name: Bromobutide), 2-(1,3-benzothiazol-2-yloxy)-N-methylacetanilide (Common name: Mefenacet), N-[3-(1-ethyl-1-methylpropyl)-1,2-oxazol-5-yl]-2,6-dimethoxybenzamide (Common name: Isoxaben), 1-(1,3-benzothiazol-2-yl)-1,3-dimethylurea (Common name: Methabenzthiazuron), 1-(1,3-benzothiazol-2-yl)-3-methylurea (Common name: Benzthiazuron), 1,1-dimethyl-3-(perhydro-4,7-methanoinden-5-yl)urea (Common name: Noruron), 3-cyclooctyl-1,1-dimethylurea (Common name: Cycluron), 1,3-dimethyl-1-(5-trifluoromethyl-1,3,4-thiazol-2-yl)urea (Common name: Thiazafluron), 1-(5-ethylsulfonyl-1,3,4-thiadiazol-2-yl)-1,3-dimethylurea (Common name: Ethidimuron), 1-[5-t-butyl-1,3,4-thiadiazol-2-yl]-1,3-dimethylurea (Common name: Tebuthiuron), 3-(5-t-butyl-1,2-oxazol-3-yl)-1,1-dimethylurea (Common name: Isouron), 3-[4-(5-t-butyl-2,3-dihydro-2-oxo-1,3,4-oxadiazol-3-yl)-3-chlorophenyl]-1,1-dimethylurea (Common name: Dimefuron), 3-(5-t-butyl-1,3,4-thiazol-2-yl)-4-hydroxy-1-methyl-2-imidazolidone (Common name: Buthidazole), 2-chloro-4,6-bis (ethylamino)-s-triazine (Common name: Simazine), 2-chloro-4-(ethylamino)-6-(isopropylamino)-s-triazine (Common name: Atrazine), 2-chloro-4,6-bis (isopropylamino)-s-triazine (Common name: Propazine), 2-chloro-4-(diethylamino)-6-(ethylamino)-s-triazine (Common name: Trietazine), 2-(t-butylamino)-4-chloro-6-(ethylamino)-s-triazine (Common name: Terbuthylazine), 2-(4-chloro-6-ethylamino-1,3,5-triazin-2-ylamino)-2methylpropionitrile (Common name: Cyanazine), 2-chloro-4-(cyclopropylamino)-6-isopropylamino-s-triazine (Common name: Cyprazine), 2-(4-chloro-6-cyclopropylamino-1,3,5-triazin-2-ylamino)-2-methylpropionitrile (Common name: Procyazin), 2-(s-butylamino)-4-(ethylamino)-6-methoxy-s-triazine (Common name: Secbumeton), 2,4-bis(isopropylamino)-6-methoxy-s-triazine (Common name: Prometon), 2,4-bis(ethylamino)-6-(methythio)-s-triazine (Common name: Simetryne), 2,4-bis(isopropylamino)-6-(methylthio)-s-triazine (Common name: Prometryne), 2-(ethylamino)-4-(isopropylamino)-6-(methythio)-s-triazine (Common name: Ametryne), 2-(t-butylamino)-4-(ethylamino)-6-(methylthio)- s-triazine (Common name: Terbutryne), 2-(isopropylamino)- 4-[(3-methoxypropyl)amino]-6-(methylthio)-s-triazine (Common name: Methoprotryne), 2-(1,2-dimethylpropylamino)-4-(ethylamino)-6-(methythio)- s-triazine (Common name: Dimethametryn), 2-(isopropylamino)-4-(methylamino)-6-(methythio)-s-triazine (Common name: Desmetryn), 4-amino-6-t-butyl-3-methylthio-1,2,4-triazin-5-(4H)-one (Common name: Metribuzin), 2-(ethylthio)-4,6-bis(isopropylamino)-s-triazine (Common name: Dipropetryn), 2-(t-butylamino)-4-(ethylamino)-6-(methoxyamino)-s-triazine (Common name: Terbumeton), 2-azido-4-(isopropylamino)-6-(methylthio)-s-triazine (Common name: Aziprotryne), 4-amino-3-methyl-6-phenyl-1,2,4-triazin-5(4H)-one (Common name: Metamitron), 6-(t-butyl-4-isobutylideneamino-3-methylthio-1,2,4-triazin-5(4H)-one (Common name: Isomethiozin), 3-cyclohexyl-6-dimethylamino-1-methyl-1,3,5-triazin-2,4(1H,3H)dione (Common name: Hexazinone), ethyl N-(4-chloro-6-ethylamino-1,3,5-triazin-2-yl)glycine (Common name: Eglinazine-ethyl), ethyl N-(4-chloro-6-isopropylamino-1,3,5-triazin-2-yl)glycine (Common name: Proglinazine-ethyl), 2-chloro-N-isopropylacetanilide (Common name: Propachlor), 2-chloro-2',6'-diethyl-N-methoxymethylacetanilide (Common name: Alachlor), N-butoxymethyl-2-chloro-2',6'-diethylacetanilide (Common name: Butachlor), 2-chloro-6'-ethyl-N-(2-methoxy-1-methylethyl) aceto-o-toluidide (Common name: Metolachlor), N,N-diallyl-2-chloroacetamide (Common name: Allidochlor), 2-chloro-N-(2-methoxyethoxy)aceto-2', 6'-xylidide (Common name: Dimethachlor), 2',4'-difluoro-2-(α,α,α-trifluoro-m-tolyloxy)nicotinanilide (Common name: Diflufenican), α,α,α-trifluoro-2,6-dinitro-N,N-dipropyl-p-toluidine (Common name: Trifluralin), N-butyl-N-ethyl-α,α,α-trifluoro-2,6-dinitro-p-toluidine (Common name: Benfluralin), N-(cyclopropylmethyl)-α,α,α-trifluoro-2,6-dinitro-N-propyl-p-toluidine (Common name: Profluralin), N,N-diethyl-2,6-dinitro-4-trifluoromethyl-m-phenylenediamine (Common name: Dinitramine), 4-isopropyl-2,6-dinitro-N,N-dipropylaniline (Common name: Isopropalin), N-s-butyl-4-t-butyl-2,6-dinitroaniline (Common name: Butralin), 4-methylsulfonyl-2,6-dinitro-N, N-dipropylaniline (Common name: Nitralin), N-(1-ethylpropyl)-2,6-dinitro-3,4-xylidine (Common name: Pendimethalin), 3,5-dinitro-N,N-dipropylsulfanylamide (Common name: Oryzalin), N-ethyl-α,α,α-trifluoro-N -(2-ethylallyl)-2,6-dinitro-p-toluidine (Common name: Ethalfluralin), 3,7-dichloroquinoline-8-carboxylic acid (Common name: Quinchlorac), 3,6-dichloropyridine-2-carboxylic acid (Common name: Clopyralid), S,S-dimethyl-2-(difluoromethyl)-4-(2-methylpropyl)-6-(trifluoromethyl)-3,5-pyridinedicarbothioate (Common name: Dithiopyr), 4-chloro-5-methylamino-2-(α,α,α-trifluoro-m-tolyl) pyridazin-3(2H)-one (Common name: Norflurazon), S-2-benzenesulfonamidoethyl O,O-diisopropylphosphorodithioate (Common name: Bensulide), (±)-2-[4,5-dihydro-4-methyl-4-(1-methylethyl)-5-oxo-1H-imidazol-2-yl]-5-ethyl-3-pyridinecarboxylic acid (Common name: Imazethapyr), (±)-2-[4,5-dihydro-4-methyl-4-(1-methylethyl)-5-oxo-1H-imidazol-2-yl]-3-quinolinecarboxylic acid (Common name: Imazaquin), methyl (±)-6-(4-isopropyl-4-methyl-5-oxo-2-imidazolin-2-yl)-m-toluate and methyl (±)-2-(4-isopropyl-4-methyl-5-oxo -2-imidazolin-2-yl)-p-toluate (Common name: Imazamethabenzmethyl), 3-[5-(1,1-dimethylethyl)-3-isoxazolyl]-4-hydroxy-1-methyl-2-imidazolidone (Common name: Busoxinone), 2-[1-(ethoxyimino)butyl]-3-hydroxy -5-(tetrahydro-2H-thiopyran-3-yl)-2-cyclohexen-1-one (Common name: Cycloxydim), and 2-[1-(ethoxyimino)propyl]-3-hydroxy-5-mesitylcyclohexen-2-one (Common name: Tralkoxydim).

The herbicidal composition for upland farming of the present invention is so selective that it exhibits an excellent herbicidal effect even at a low dosage on various weeds in upland farming, in particular, a wide variety of weeds in fields of crops such as wheat and barley, but is harmless to the crops.

The herbicidal composition for upland farming of the present invention has an excellent herbicidal effect on various weeds in upland farming, in particular, weeds in fields of crops such as wheat and barley, for example, dicotyledons such as cleavers (*Galium aparine*), chickweed (*Stellaria media*), birdseye speed-well (*Veronica persica*), violet (*Viola arvensis*), sentless chamomile (*Matricaria inodora*), field pennycress (*Thlaspi arvense*), pineapple weed (*Matricaria matricarioides*), charlock (*Sinapis arrensis*), purple deadnettle (*Lamium purpureum*), creeping thistle (*Cirsium arvense*), forget-me-not (*Myosotis scorpioides*), lady's thumb (*Polygonum persicaria*), pale persicaria (*Polygonum scabrum*), sticky chickweed (*Cerastium* viscosum), black bindweed (*Polygonum convolvulus*), field bindweed (*Convolvulus arvensis*), common lambsquarters (*Chenopodium album*), redroot pigweed (*Amaranthus retroflexus*), and black nightshade (*Solanum nigrum*). Furthermore, said composition is effective also in controlling gramineous weeds such as windgrass (*Apera spicaventi*), water foxtail (*Alopecurus aequalis*), etc.

The herbicidal composition for upland farming of the present invention can control, in particular, weeds which have been difficult to control, for example, cleavers, chickweed, birdseye speedwell, sentless chamomile, field pennycress, lady's thumb, pale persicaria, black bindweed, etc. at the same time.

For applying the herbicidal composition for upland farming of the present invention, it may be prepared into suitable forms according to an ordinary manner for preparation of agrochemicals, depending on purposes. For example, said composition is blended with one or more materials selected from the group consisting of solid carriers, liquid carriers and surfactants, and optionally adjuvants, etc. and prepared into a preparation form such as granules, a wettable powder, dust, a suspension concentrate, a soluble concentrate, or the like.

The active ingredients of the herbicidal composition for upland farming of the present invention may be blended in optional proportions, depending on the type of formulation. The blending proportions of the active ingredients in said composition are as follows. The 3-substituted phenylpyrazole derivative of the general formula (I) and the sulfonylurea derivative(s) may be blended in optional proportions. Usually, the proportion of the sulfonylurea derivative(s) may be chosen in the range of 0.01 to 100 parts by weight, preferably 0.05 to 50 parts by weight, per part by weight of the 3-substituted phenylpyrazole derivative of the general formula (I). The proportion of the phenylurea derivative(s) may be chosen in the range of 1 to 5,000 parts by weight, preferably 5 to 1,000 parts by weight, per part by weight of the 3-substituted phenylpyrazole derivative. The proportion of the phenoxy fatty acid derivative(s) may be chosen in the range of 1 to 1,000 parts by weight, preferably 1 to 500 parts by weight, per part by weight of the 3-substituted phenylpyrazole derivative.

For example, when applied to a wheat field, the herbicidal composition for upland farming of the present invention is applied preferably during the early-post emergence or vegetative growth stage of wheat and weeds. But, the application time of the composition is not limited to these periods and the composition may be applied to soil before the emergence of wheat and weeds.

The dosage of the herbicidal composition for upland farming of the present invention may be chosen in the range of 0.1 to 6,000 g (in terms of the active ingredients) per hectare.

Typical examples of the present invention are described below but they should not be construed as limiting the scope of the invention.

In the examples, parts are all by weight.

EXAMPLE 1

| | |
|---|---|
| Compound 1 | 0.1 part |
| Compound A-1 | 0.2 part |
| Dioctyl sulfosuccinate sodium salt | 0.3 part |
| Sodium polyacrylate | 2.0 parts |
| Bentonite | 35.0 parts |
| Clay | 62.4 parts |

Granules were prepared by mixing uniformly and grinding the above ingredients, and kneading the resulting mixture together with a suitable amount of water, followed by granulation and drying.

EXAMPLE 2

| | |
|---|---|
| Compound 7 | 0.2 part |
| Compound A-1 | 0.1 part |
| Dioctyl sulfosuccinate sodium salt | 0.3 part |
| Sodium polyacrylate | 2.0 parts |
| Bentonite | 35.0 parts |
| Clay | 62.4 parts |

Granules were prepared by mixing uniformly and grinding the above ingredients, and kneading the resulting mixture together with a suitable amount of water, followed by granulation and drying.

EXAMPLES 3 to 5

Granules were prepared according to each recipe shown in Table 2, in the same manner as in Examples 1 and 2.

TABLE 2

| | Example 3 | Example 4 | Example 5 |
|---|---|---|---|
| Compound 5 | 0.5 | — | — |
| Compound 7 | — | 1.0 | 0.5 |
| Compound A-3 | — | — | 0.5 |
| Compound B-1 | 2.0 | — | — |
| Compound C-1 | — | 8.0 | — |
| Finely divided hydrated silica | 1.0 | 2.0 | 1.0 |
| Poly(vinyl alcohol) | 0.5 | 0.5 | 0.5 |
| Silica sand | 96.0 | 88.5 | 97.5 |
| Total | 100.0 | 100.0 | 100.0 |

EXAMPLE 6

| | |
|---|---|
| Compound 7 | 5.0 parts |
| Compound A-1 | 7.0 parts |
| Polyoxyethylene nonyl phenyl ether | 3.0 parts |
| Calcium ligninsulfonate | 3.0 parts |
| Finely divided hydrated silica | 4.0 parts |
| Powdered calcium carbonate | 78.0 parts |

A wettable powder was prepared by mixing uniformly and grinding the above ingredients.

EXAMPLE 7

| | |
|---|---|
| Compound 9 | 10.0 parts |
| Compound A-1 | 5.0 parts |
| Polyoxyethylene nonyl phenyl ether | 3.0 parts |
| Calcium ligninsulfonate | 3.0 parts |
| Finely divided hydrated silica | 2.0 parts |
| Powdered calcium carbonate | 77.0 parts |

A wettable powder was prepared by mixing uniformly and grinding the above ingredients.

EXAMPLES 8 to 10

Wettable powders were prepared according to each recipe shown in Table 3, in the same manner as in Examples 6 and 7.

TABLE 3

|  | Example 8 | Example 9 | Example 10 |
| --- | --- | --- | --- |
| Compound 1 | — | 5.0 | — |
| Compound 7 | 20.0 | — | 10.0 |
| Compound A-3 | — | 7.0 | — |
| Compound B-1 | 40.0 | — | — |
| Compound C-1 | — | — | 20.0 |
| Sidium lauryl sulfate | 3.0 | 3.0 | 3.0 |
| Calcium lignin sulfonate | 3.0 | 3.0 | 3.0 |
| Finely divided hydrated silica | 7.0 | 4.0 | 5.0 |
| Clay powder | 27.0 | 78.0 | 59.0 |
| Total | 100.0 | 100.0 | 100.0 |

EXAMPLE 11

| Compound 7 | 6.0 parts |
| --- | --- |
| Compound A-1 | 6.0 parts |
| Polyoxyethylene nonyl phenyl ether | 1.5 parts |
| Polyoxyethylene styryl phenyl ether | 1.5 parts |
| Xanthan gum | 0.2 part |
| Water | 84.8 parts |

A suspension concentrate was prepared by mixing the above ingredients uniformly, followed by wet grinding.

EXAMPLE 12

| Compound 9 | 3.0 parts |
| --- | --- |
| Compound A-1 | 10.0 parts |
| Polyoxyethylene nonyl phenyl ether | 1.5 parts |
| Polyoxyethylene styryl phenyl ether | 1.5 parts |
| Xanthan gum | 0.2 part |
| Water | 83.8 parts |

A suspension concentrate was prepared by mixing the above ingredients uniformly, followed by wet grinding.

EXAMPLES 13 to 14

Suspension concentrates were prepared according to each recipe shown in Table 4, in the same manner as in Examples 11 and 12.

TABLE 4

|  | Example 13 | Example 14 |
| --- | --- | --- |
| Compound 1 | 5.0 | — |
| Compound 7 | — | 3.0 |
| Compound A-3 | — | 3.0 |
| Compound B-1 | 15.0 | — |
| Compound C-1 | — | — |
| Polyoxyethylene nonyl phenyl ether | 1.5 | 1.5 |
| Polyoxyethylene styrene phenyl ether | 1.5 | 1.5 |
| Xantan gum | 0.2 | 0.2 |
| Ethylene glycol | 5.0 | 5.0 |
| Water | 71.8 | 85.8 |
| Total | 100.0 | 100.0 |

TEST EXAMPLE 1

Synergistic-effect test on compositions of the present invention

A pot with a diameter of 12 cm and a height of 11 cm was filled with upland soil and seeded with birdseye speedwell (*Veronica persica*) so as to adjust the depth of covering soil to 0.5 cm, and the birdseye speedwell was grown in a greenhouse.

When the birdseye speedwell was grown to a leaf stage of 2 and a height of 3 cm, a predetermined amount of each of various herbicidal compositions of the present invention was diluted with water and the dilution was sprayed from above uniformly on the whole surfaces of the stem and leaves in a spray volume of 500 liters per hectare by the use of a laboratory sprayer. On 21 days after the spraying, the degree of growth of the above-ground part of surviving birdseye speedwell plants was visually judged in the range of zero (ineffective) to 100 (complete kill). The test results obtained are shown in Tables 5 to 7.

TABLE 5

| | Amount of Compound 7 as active ingredient (g/ha) | | | | | |
| --- | --- | --- | --- | --- | --- | --- |
| | 0 | 0.8 | 1.5 | 3.0 | 6.0 | 12.0 |
| Amount of compound A-1 as active ingredient (g/ha) 0 | 0 | 30 | 50 | 70 | 85 | 95 |
| 0.8 | 40 | 50 | 60 | 70 | 90 | 98 |
| 1.5 | 50 | 60 | 70 | 85 | 93 | 99 |
| 3.0 | 60 | 70 | 80 | 90 | 95 | 100 |
| 6.0 | 80 | 85 | 90 | 95 | 98 | 100 |
| 12.0 | 90 | 93 | 95 | 98 | 100 | 100 |

TABLE 6

| | Amount of Compound 7 as active ingredient (g/ha) | | | | | |
| --- | --- | --- | --- | --- | --- | --- |
| | 0 | 0.8 | 1.5 | 3.0 | 6.0 | 12.0 |
| Amount of compound B-1 as active ingredient (g/ha) 0 | 0 | 30 | 50 | 70 | 85 | 95 |
| 63 | 0 | 30 | 55 | 75 | 90 | 98 |
| 125 | 0 | 35 | 60 | 80 | 95 | 98 |
| 250 | 0 | 45 | 70 | 83 | 97 | 99 |
| 500 | 0 | 50 | 80 | 85 | 98 | 100 |
| 1000 | 10 | 60 | 85 | 90 | 99 | 100 |

TABLE 7

| | Amount of Compound 7 as active ingredient (g/ha) | | | | | |
| --- | --- | --- | --- | --- | --- | --- |
| | 0 | 0.8 | 1.5 | 3.0 | 6.0 | 12.0 |
| Amount of compound C-1 as active ingredient (g/ha) 0 | 0 | 30 | 50 | 70 | 85 | 95 |
| 63 | 40 | 50 | 70 | 85 | 93 | 98 |
| 125 | 60 | 65 | 80 | 90 | 95 | 99 |
| 250 | 70 | 75 | 85 | 93 | 98 | 100 |
| 500 | 75 | 85 | 90 | 95 | 98 | 100 |
| 1000 | 90 | 93 | 98 | 98 | 99 | 100 |

The above results are shown in the drawings for facilitating the understanding.

FIG. 1 is a graph obtained by isobole analysis on the basis of the herbicidal effect on birdseye speedwell shown in Table 5 in the test example.

The axis of abscissa refers to the amount (g/ha) of compound 7 as active ingredient and the axis of ordinate to the amount (g/ha) of compound A-1 as active ingredient.

The expected ED 90 isobole of additive effect is shown in the broken line and ED 90 isobole of the combination between compound 7 and compound A-1 obtained in practice is shown in the solid line.

Figure 2:
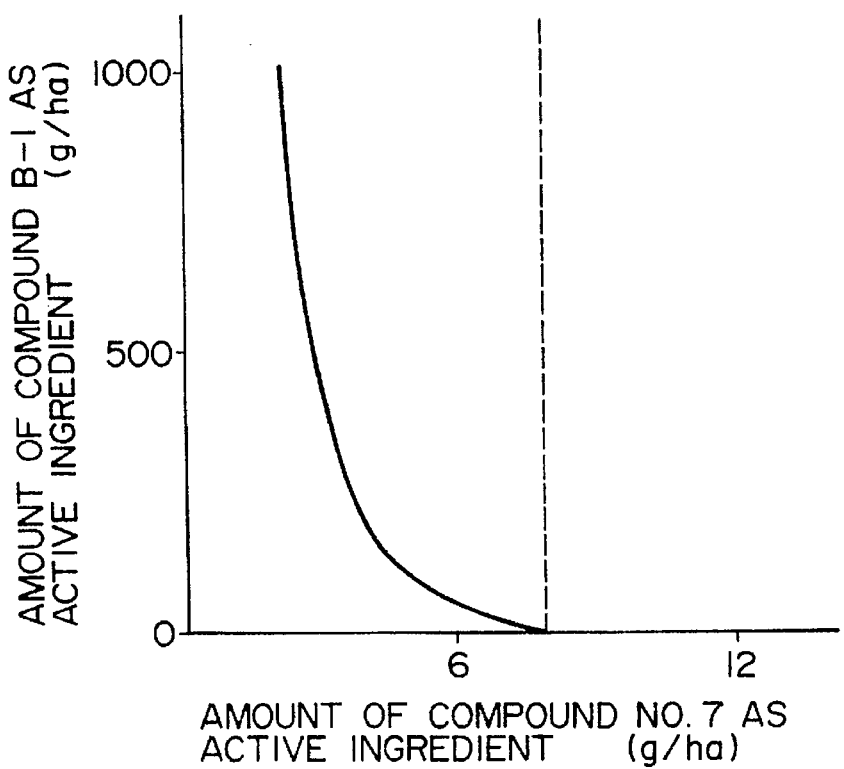
FIG. 2 is a graph illustrating the results shown in Table 6, by isobole analysis.
Figure 3:
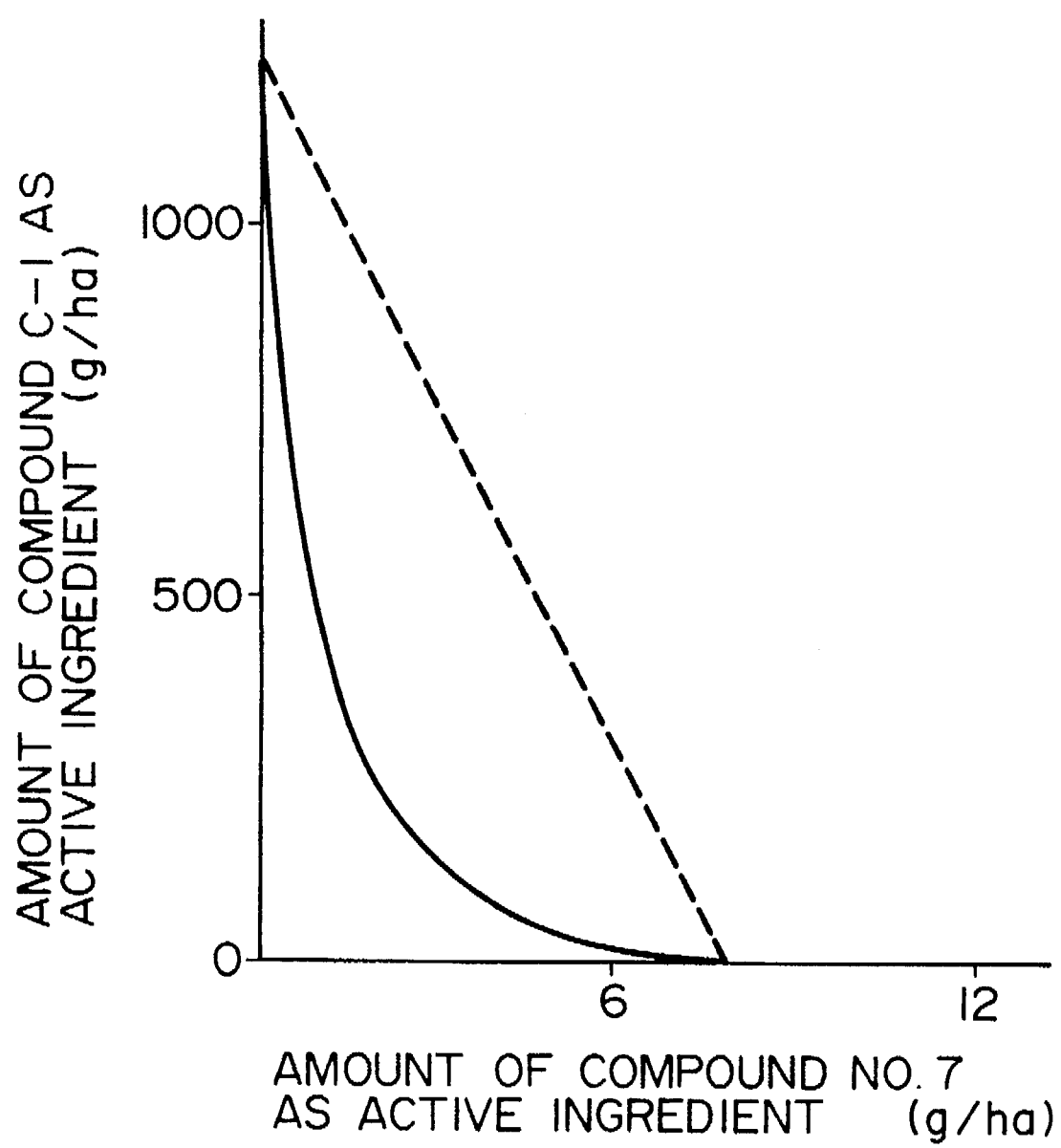
FIG. 3 is a graph illustrating the results shown in Table 7, by isobole analysis.

FIGS. 2 and 3 are graphs obtained in the same manner as in FIG. 1 on the basis of the results shown in Tables 6 and 7, respectively.

As shown in FIGS. 1 to 3, the herbicidal compositions for upland farming of the present invention have synergistic effect clearly.

What is claimed is:

1. A herbicidal composition for upland farming which comprises as active ingredients a synergistically effective amount of a 3-substituted phenylpyrazole derivative represented by the general formula (I):

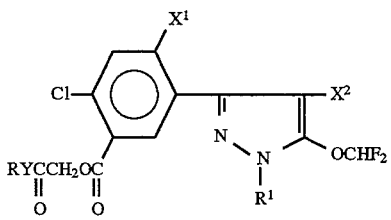

(wherein R is a hydrogen atom, a $C_{1-6}$ alkyl group, a $C_{3-6}$ cycloalkyl group, a $C_{1-6}$ haloalkyl group, a $C_{2-6}$ alkenyl group or a $C_{2-6}$ alkynyl group, $R^1$ is a $C_{1-6}$ alkyl group, $X^1$ and $X^2$, which may be the same or different, are halogen atoms, and Y is an oxygen atom or a sulfur atom) and at least one compound selected from the group consisting of sulfonylurea derivatives, phenylurea derivatives and phenoxy fatty acid derivatives.

2. A herbicidal composition for upland farming according to claim 1, wherein as the compound(s) selected, at least one sulfonylurea derivative is selected from the group consisting of methyl 2-(4-methoxy-6-methyl-1,3,5-triazin-2-ylcarbamoylsulfamoyl)benzoate, 1-(2-chlorophenylsulfonyl)-3-(4-methoxy-6-methyl-1,3,5-triazin-2-yl)urea, methyl 3-(4-methoxy-6-methyl-1,3,5-triazin-2-ylcarbamoylsulfamoyl)-thiophen-2-carboxylate, methyl 2-[4-methoxy-6-methyl-1,3,5-triazin-2-yl(methyl) carbamoylsulfamoyl]benzoate, and 1-[2-(2-chloroethoxy) phenylsulfonyl]-3-(4-methoxy-6-methyl-1,3,5-triazin-2-yl) urea.

3. A herbicidal composition for upland farming according to claim 1, wherein as the compound(s) selected, at least one phenylurea derivative is selected from the group consisting of 3-p-cumenyl-1,1-dimethylurea, 3-(3,4-dichlorophenyl)-1,1-dimethylurea, 3-(3,4-dichlorophenyl)-1-methoxy-1-methylurea, 3-(4-chlorophenyl)-1,1-dimethylurea, and 3-(3-chloro-p-tolyl)-1,1-dimethylurea.

4. A herbicidal composition for upland farming according to claim 1, wherein as the compound(s) selected, at least one phenoxy fatty acid derivatives is selected from the group consisting of 4-chloro-o-tolyloxyacetic acid or sodium or potassium salt thereof, ethyl 4-chloro-o-tolyloxyacetate, butyl 4-chloro-o-tolyloxyacetate, 4-chloro-o-tolyloxypropionic acid or potassium or diethanolamine salt thereof, and 4-chloro-o-tolyloxybutyric acid or sodium salt thereof.

5. A herbicidal composition for upland farming according to claim 1, wherein the sulfonylurea derivative is contained in an amount of 0.01 to 100 parts by weight per part by weight of the 3-substituted phenylpyrazole derivative of the general formula (I), and the phenylurea derivative or the phenoxy fatty acid derivatives is contained in an amount of 1 to 5,000 parts by weight per part by weight of said derivative.

6. A herbicidal composition for upland farming according to claim 5, which is for wheat, barley, oats and rye.

7. A method for controlling weeds in upland farming which comprises applying a synergistically effective amount of a herbicidal composition in a dosage chosen in the range of 0.1 to 6,000 g, in terms of the active ingredients of the composition, per hectare for controlling weeds undesirable for the growth of upland crops, said herbicidal composition comprising as active ingredients:

a 3-substituted phenylpyrazole derivative represented by the general formula (I):

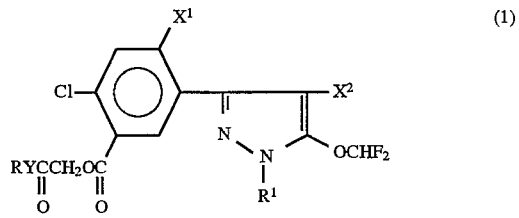

wherein R is a hydrogen atom, a $C_{1-6}$ alkyl group, a $C_{3-6}$ cycloalkyl group, a $C_{1-6}$ haloalkyl group, a $C_{2-6}$ alkenyl group or a $C_{2-6}$ alkynyl group, $R^1$ is a $C_{1-6}$ alkyl group, $X^1$ and $X^2$, which may be the same or different, are halogen atoms, and Y is an oxygen atom or a sulfur atom; and at least one compound selected from the group consisting of sulfonylurea derivatives, phenylurea derivatives and phenoxy fatty acid derivatives.

8. A method for controlling weeds in upland farming according to claim 7, wherein as the compound(s) selected, at least one sulfonylurea derivative is selected from the group consisting of methyl 2-(4-methoxy-6-methyl-1,3,5-triazin-2-ylcarbamoylsulfamoyl)benzoate, 1-(2-chlorophenylsulfonyl)-3-(4-methoxy-6-methyl-1,3,5-triazin-2-yl)urea, methyl 3-(4-methoxy-6-methyl-1,3,5-triazin-2-ylcarbamoylsulfamoyl)-thiophen-2-carboxylate, methyl 2-[4-methoxy-6-methyl-1,3,5-triazin-2-yl(methyl) carbamoylsulfamoyl]benzoate, and 1-[2-(2-chloroethoxy) phenylsulfonyl]-3-(4-methoxy-6-methyl-1,3,5-triazin-2-yl) urea.

9. A method for controlling weeds in upland farming according to claim 7, wherein as the compound(s) selected, at least one phenylurea derivative is selected from the group consisting of 3-p-cumenyl-1,1-dimethylurea, 3-(3,4-dichlorophenyl)-1,1-dimethylurea, 3-(3,4-dichlorophenyl)-1-methoxy-1-methylurea, 3-(4-chlorophenyl)-1,1-dimethylurea, and 3-(3-chloro-p-tolyl)-1,1-dimethylurea.

10. A method for controlling weeds in upland farming according to claim 7, wherein as the compound(s) selected, at least one phenoxy fatty acid derivative is selected from the group consisting of 4-chloro-o-tolyloxyacetic acid or sodium or potassium salt thereof, ethyl 4-chloro-o-tolyloxyacetate, butyl 4-chloro-o-tolyloxyacetate, 4-chloro-o-tolyloxypropionic acid or potassium or diethanolamine salt thereof, and 4-chloro-o-tolyloxybutyric acid or sodium salt thereof.

11. A method for controlling weeds in upland farming according to claim 7, wherein the upland crop is wheat.

12. A method for controlling weeds in upland farming according to claim 11, wherein the herbicidal composition is applied during the early-post emergence or vegetative growth stage of the upland crop and weeds.

* * * * *

UNITED STATES PATENT AND TRADEMARK OFFICE
CERTIFICATE OF CORRECTION

PATENT NO. : 5,635,448
DATED : June 3, 1997
INVENTOR(S) : Tsutomu Mabuchi, et al.

It is certified that error appears in the above-identified patent and that said Letters Patent is hereby corrected as shown below:

On the title page, item [73] Assignee, should read-- Nihon Nohyaku Co., Ltd.
1-2-5 Nihonbashi, Chuo-Ku, Tokyo, Japan--.

Signed and Sealed this

Thirtieth Day of December, 1997

Attest:

BRUCE LEHMAN

*Attesting Officer*     Commissioner of Patents and Trademarks